(12) United States Patent
Bright

(10) Patent No.: US 9,119,603 B2
(45) Date of Patent: Sep. 1, 2015

(54) TUNNELLING INSTRUMENT FOR SUBCUTANEOUSLY PLACING AN ARTICLE, AND METHOD OF USE OF SAID INSTRUMENT

(75) Inventor: Charles Bright, Burton-on-Trent (GB)

(73) Assignee: PLASMED LTD., Staffordshire, Burton-On-Trent (GB)

( * ) Notice: Subject to any disclaimer, the term of this patent is extended or adjusted under 35 U.S.C. 154(b) by 1500 days.

(21) Appl. No.: 12/297,357

(22) PCT Filed: Apr. 18, 2007

(86) PCT No.: PCT/GB2007/001395
§ 371 (c)(1),
(2), (4) Date: Dec. 30, 2008

(87) PCT Pub. No.: WO2007/119060
PCT Pub. Date: Oct. 25, 2007

(65) Prior Publication Data
US 2009/0299377 A1  Dec. 3, 2009

(30) Foreign Application Priority Data

Apr. 18, 2006  (GB) .................................. 0607547.7

(51) Int. Cl.
*A61B 17/00* (2006.01)
*A61M 25/01* (2006.01)
*A61B 17/34* (2006.01)
*A61B 17/32* (2006.01)

(52) U.S. Cl.
CPC ...... *A61B 17/00234* (2013.01); *A61M 25/0136* (2013.01); *A61M 25/0194* (2013.01); *A61B 17/3468* (2013.01); *A61B 2017/320044* (2013.01)

(58) Field of Classification Search
CPC ..................... A61M 25/0194; A61M 25/0069; A61M 25/0136; A61B 17/3468; A61B 17/00234; A61B 2017/320056; A61B 2017/320044
USPC .................................. 606/108, 190, 222, 223
See application file for complete search history.

(56) References Cited

U.S. PATENT DOCUMENTS

| | | | | |
|---|---|---|---|---|
| 4,431,426 A | * | 2/1984 | Groshong et al. | 604/523 |
| 4,832,687 A | * | 5/1989 | Smith, III | 604/506 |
| 5,061,245 A | * | 10/1991 | Waldvogel | 604/170.01 |
| 5,306,240 A | * | 4/1994 | Berry | 604/507 |
| 6,475,139 B1 | * | 11/2002 | Miller | 600/135 |
| 7,628,795 B2 | * | 12/2009 | Karwoski et al. | 606/108 |

* cited by examiner

*Primary Examiner* — Katherine Rodjom
(74) *Attorney, Agent, or Firm* — Andrus Intellectual Property Law, LLP

(57) ABSTRACT

An improved tip and handle for a tunnelling instrument are provided along with an improved tunnelling instrument. The tip is configured for attachment to a tunnelling instrument and includes a first portion configured to form a tunnel, a second portion sized to fit within a tubular component to be placed in the tunnel, and a third portion configured for attachment of the tubular component. The handle is configured to be attached to and detached from a tunneller shaft of a tunnelling instrument, at any point along the length of the tunneller shaft. The tunnelling instrument comprises a pair of tips, a connection means for forming a link between the tips, and a tunneller shaft slidably engagable with the connection means and attachable to either of the tips. Various forms of use of the tunnelling instrument are also disclosed.

14 Claims, 10 Drawing Sheets

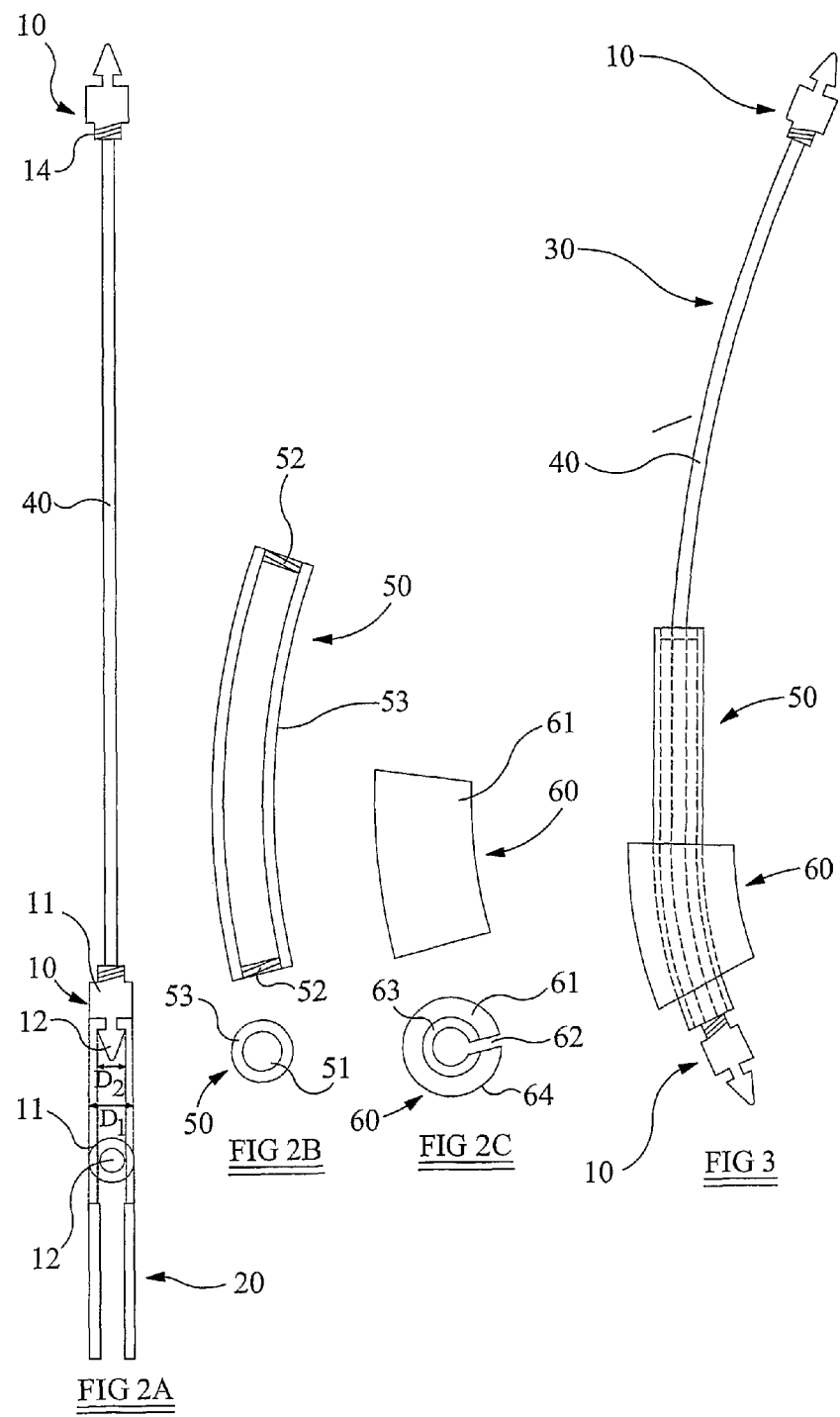

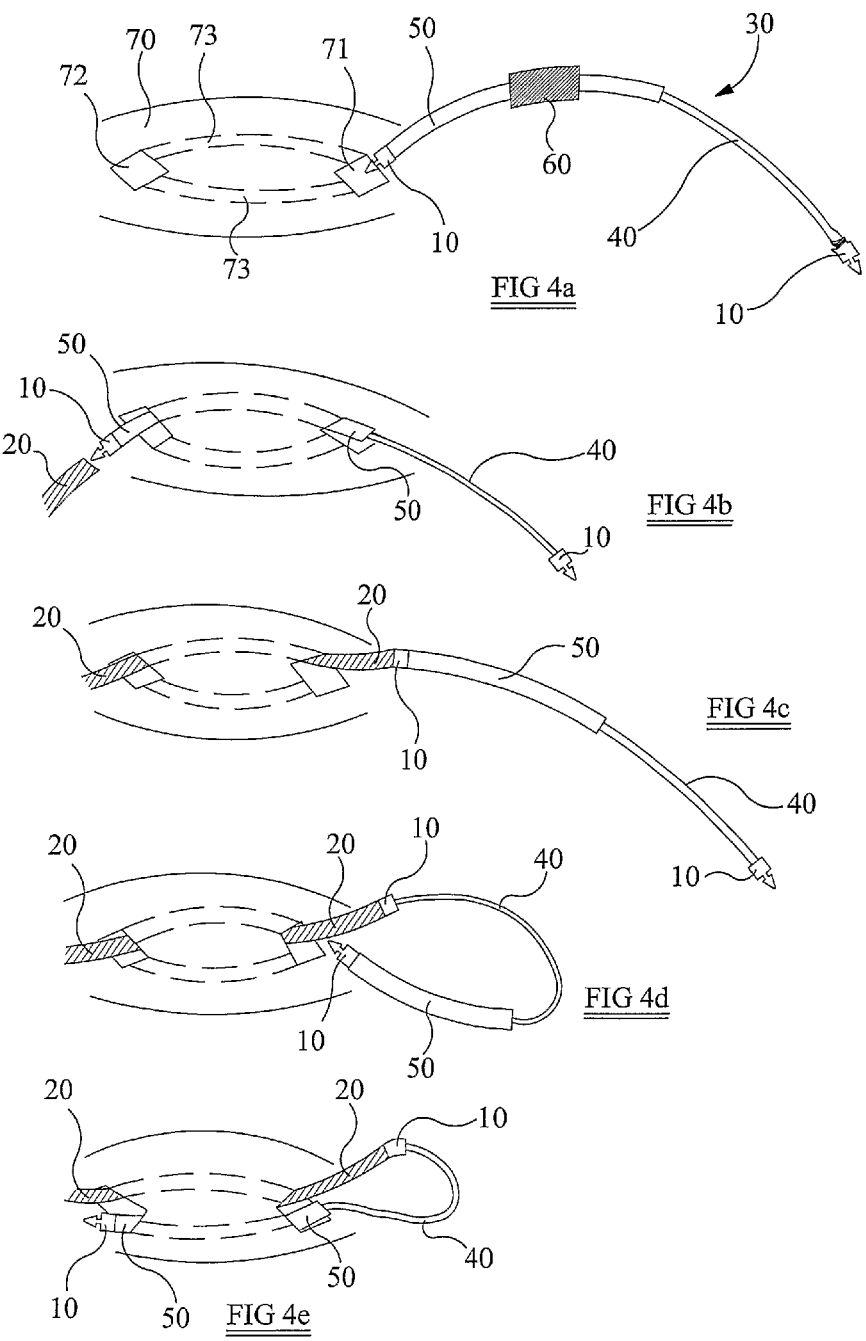

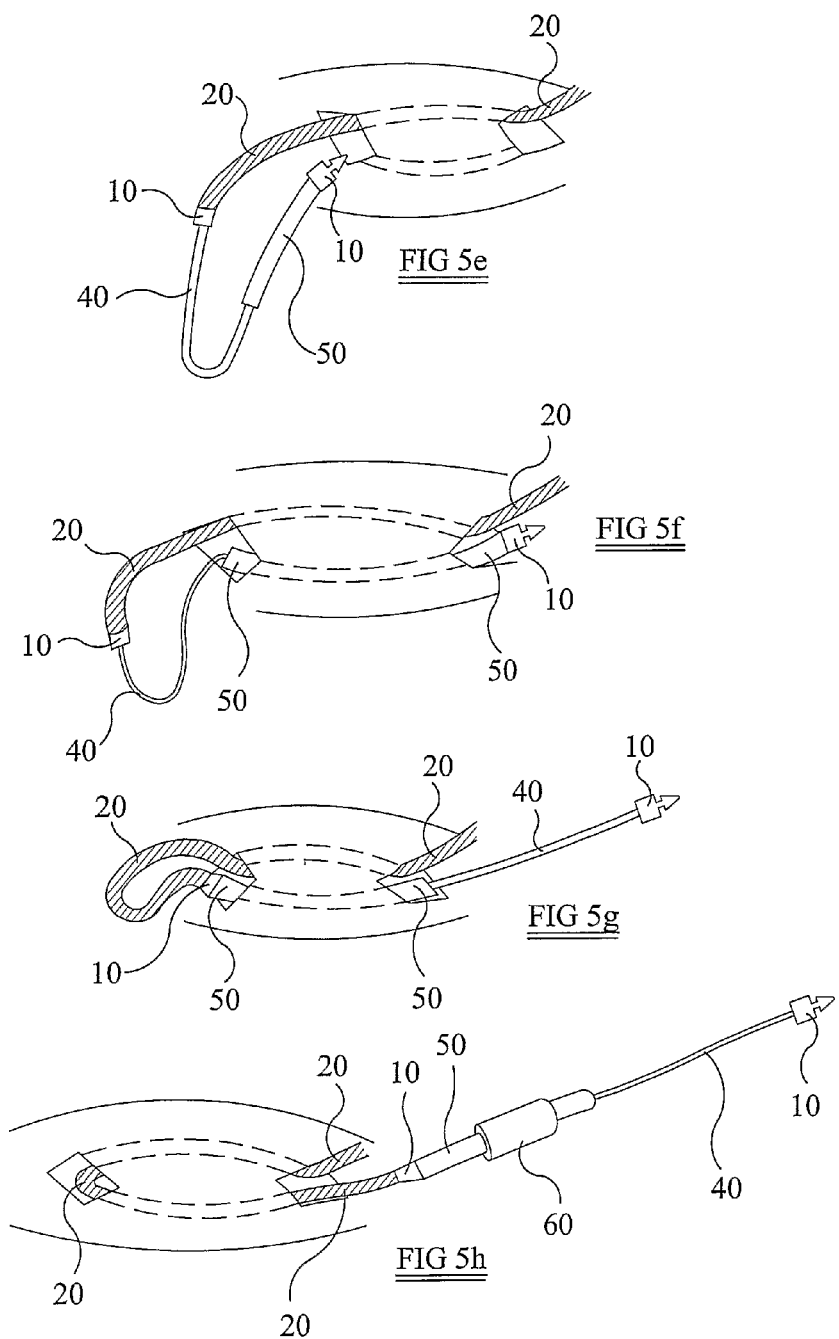

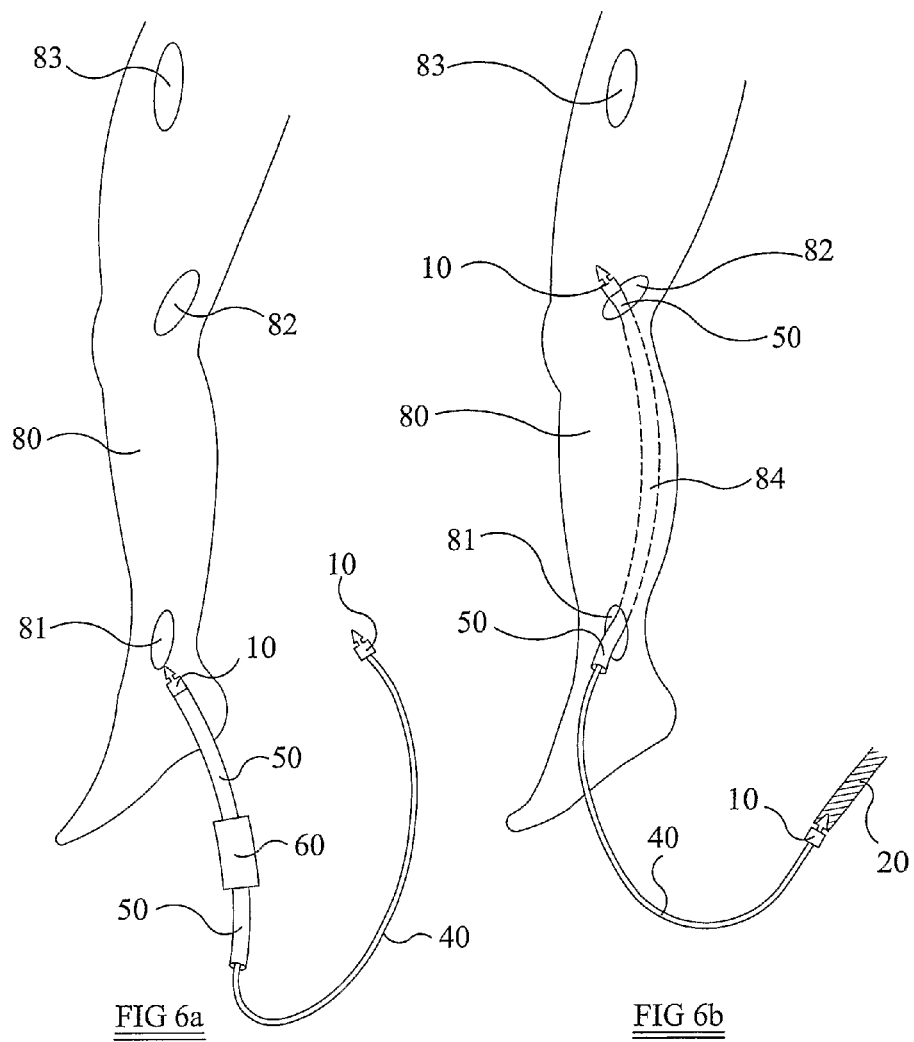

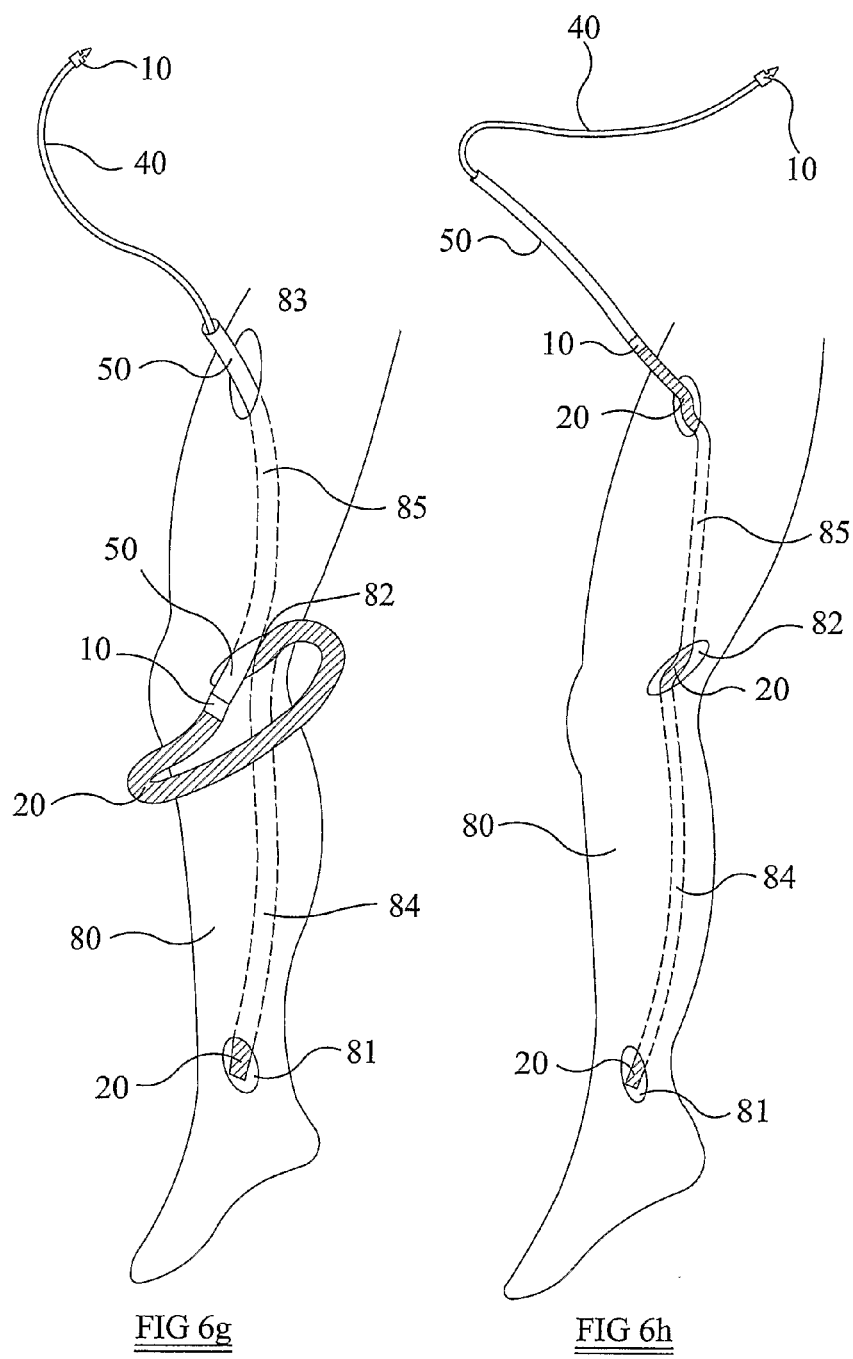

TUNNELLING INSTRUMENT FOR SUBCUTANEOUSLY PLACING AN ARTICLE, AND METHOD OF USE OF SAID INSTRUMENT

This invention relates to a tunnelling instrument for producing a subcutaneous tunnel between skin and muscle or tissue of a patient, the tunnel extending between respective positions in the patient's body in order to place an article, such as a graft or catheter in a minimally invasive manner. The invention also relates to a method of use of said instrument.

An example of use for a known tunnelling instrument would be the placing of a vascular graft to bypass a diseased vessel or to act as a conduit between an artery and vein for vascular access haemodialysis purposes. Generally the tunnelling instrument would consist of a straight or curved rod made of rigid material, such as steel, with a handle on one end and a blunt tip on the other end. The width of the blunt tip employed would approximate to the internal diameter of the required tunnel, which is ideally equivalent to the outer diameter of the tubular article to be placed in the tunnel.

During the tunnelling procedure, two incisions would typically be made and the tunnelling instrument introduced, tip first, into the first incision. The instrument would then be pushed subcutaneously towards the second incision, moving through the tissue by blunt dissection until the tip exits from the second incision site. The tip would then be changed by unscrewing it from the instrument rod, and replaced with a smaller tip representative of the internal diameter of the tubular article to be placed subcutaneously. The end of the tubular article would then be pushed over the tip, and attached by suture material, before the article is pulled back through the newly made tunnel. The tubular article is then detached from the tip of the instrument and the respective ends of the article can be anastomosed to the necessary anatomical structures at each end. More than one tunnel can often be necessary in the placement of a vascular prosthesis or catheter.

A first type of tunnelling instrument for subcutaneously placing a tubular article consists of a rigid shaft device with a removable bullet tip on one end, and a fixed handle on its other end. The bullet tips are available in various diameters, and the tip diameter chosen to produce the tunnel will often be representative of the external diameter of the tubular article to be subcutaneously placed. During a procedure, at least two incisions will be made, and the tunnelling instrument introduced, tip first, into the incision, and pushed subcutaneously towards the second incision, where the tip will emerge. The emergent tip is then replaced by unscrewing it from the rigid shaft and screwing onto the shaft in its place a tip of smaller diameter, normally representative of the internal diameter of the tubular article. The article is pushed over the new tip and attached by suture material, before being pulled back through the newly made tunnel, from exit to entry incision site. If more than one tunnel is required, then the tubular article may be cut from the tunnelling tip, and the originally sized tunnelling tip placed on the end of the rigid shaft for a repeat of the above procedure.

A second type of tunnelling instrument for subcutaneously placing a tubular article is similar to said first type, but differs in that the handle is of a removable design, so that the tips and the handle are interchangeable to either end of the rigid shaft, thereby allowing the instrument to be used in a bi-directional manner. This means that after the tunnelling tip emerges at the second incision site, as described above, this tip is replaced by the handle from the opposite end of the shaft, with the smaller diameter tip now being attached to the end of the rigid shaft at the first incision site, i.e. from where the handle has been unscrewed. The tubular article is then attached, as described above, to the tip, and pulled through the tunnel by means of the handle, from the first to the second incision site. This type of instrument is disclosed in U.S. Pat. No. 5,306,240.

A third type of tunnelling instrument for subcutaneously placing a tubular article consists of a straight or curved hollow tube with a rigid inner rod. The instrument again utilises a removable handle and removable bullet tips. The tunnelling action is similar to that described with the bi-directional instrument, except that after the tunnel has been produced, the hollow tube remains in place while the handle is interchanged with the tip, which is replaced by a smaller tip. The tubular article is then attached to the new tip and pulled through the inside of the hollow tube. Once the article is in place, the hollow tube of the tunnelling instrument is extracted from the tunnel, leaving the article in place. One version of this instrument utilises a disposable plastics material hollow tube as the tunnelling tube, instead of a metal re-usable and re-sterilizable type. This utilisation of a hollow tunnelling tube or sheath is disclosed in U.S. Pat. No. 5,061,245.

As far as the use of said known instruments are concerned, it is generally established that there are significant clinical benefits in having the tunnel diameter matched to that of the tubular article, such as a tubular graft. If the tunnel is undersized relative to the external diameter of the tubular graft, then trauma will be caused to the tissues inside the tunnel when the graft of consequently larger diameter is pulled through the smaller diameter tunnel. Moreover, if the tunnel is undersized more radial pressure is likely to be placed on the inner walls of the tubular graft by the smaller diameter tunnel. If, on the other hand, the tunnel is oversized, then there will typically be gaps between the graft and the tissues inside the tunnel, and this potentially will continue along the whole length of the graft within the tunnel. This can lead to various serious complications, including; a greatly reduced rate of healing and incorporation of the graft; the formation of seroma from the wall of the graft (sweating of the graft); an increased risk of infection; and painful swelling of the area.

The first type of the known instruments referred to above is clearly disadvantageous in having a fixed handle, in that this allows the article to be placed via one direction, namely pulled back through the tunnel. It is thus uni-directional. There is a clinical desirably to be able to tunnel in either of two directions, one reason being so that there is less trauma caused on the inside of the tunnel when the tunnelling shaft travels only one way, namely entrance through to exit, as opposed to going back through the tunnel a second time with the rigid tunneller in the opposite direction.

Although the second type of known instrument is bi-directional, the handle, the tunnelling tip and the tubular article attachment tip require frequent changing, which is time consuming and thus undesirably lengthens the time of the operation. Also, attaching the tubular article to the conventional bullet tip can cause the article to stand proud of the tip diameter, so that the act of pulling the article through the tunnel often results in the ends of the attached article to plough through the tunnel and cause trauma to the inside thereof. This is also a factor with the first type of known instrument.

When creating a further tunnel during the same procedure, it is known to cut back the tubular article from the respective attachment bullet tip before changing back to using the tunnelling tip for the creation of the next tunnel. This requires the operator subsequently to have to reattach the end of the tubular article to the attachment tip for placement in the next tunnel, again causing undesirable delay to the operation procedure. Other operators try to save reattachment time described above by unscrewing the attachment tip from the shaft with the tubular article still attached when wanting to revert to reconnecting the tunnelling tip for the creation of the next tunnel, before replacing that with the attachment tip with the tubular article still attached to the attachment tip back onto the tunnelling shaft prior to pulling the article through the next tunnel. This action consequently risks the twisting of the tubular article. Such twisting is contradicted and can lead to serious problems.

Frequently in practice, the wrong sized bullet tip is used in producing the tunnel, as firstly it is not always easy visually to recognise small differences in tip diameters, and secondly the specifically sized tip may be missing from the surgical tray. This leads to the production of incorrectly sized tunnels. Some tubular grafts have, as part of their design, different internal and external diameters from one end to the other. They may for example have an internal diameter of 6 mm at one end and an internal diameter of 8 mm at the other end. A reason for this can be to enable important flow restrictions. Some tubular articles, such as externally supported vascular prosthetics, can demand greater diameter tunnels than unsupported devices. These demands complicate tip choice, as well as tunnelling directional choices.

The third type of known instrument creates a significantly oversized tunnel because of the extra diameter necessary to allow the tubular article to be pulled through the hollow tube. It is also sometimes difficult to remove the hollow tube from the surgical tunnel once the tubular article is in place, and can easily cause more trauma to the tissues inside the tunnel on removal.

None of the three above mentioned known types of instrument can easily deal with the tunnelling of longer tubular grafts and catheters, because of the physical constraints of their designs and their inherent requirement for bullet tip changes and handle changes. The rigid rod or tube type tunneller does not allow for the easy placement of a long continuous tubular device or catheter in more than one single tunnel, because it is often constrained by its rigidity, and furthermore the development of alternative operative techniques of tubular graft placement are restricted by these shortcomings in tunneller design. Another problem is that all of the designs are mostly reusable metal instruments and as such require cleaning and resterilization prior to reuse.

Finally, it is sometimes very important to tunnel into the body from distal to proximal in order to find the correct subcutaneous plane for the tubular article to lie. This leads to more complicated directional choices in tunnelling technique and frequent changes in tunneller handle and the various sized tips with respect to the tunneller shaft.

An object of the invention is to provide a tunnelling instrument which enables at least some of the abovementioned disadvantages to be overcome. A further object is to provide an improved method of subcutaneous placement using said instrument.

DISCLOSURE OF INVENTION

In accordance with a first aspect of the present invention there is provided a tip for a tunnelling instrument, said tip comprising: an attachment means for attaching said tip to a tunnelling instrument; a first portion proximal to said attachment means and having the greatest diameter of said tip; a second portion distal to said attachment means and having a maximum diameter of less than said first portion; and a third portion disposed between said first portion and said second portion and having a diameter of less than or equal to said second portion.

This particular tip construction has the advantage that the same tip can be used for the creation of a tunnel, whereby the diameter of the tunnel is approximately equal to the maximum diameter of the first portion, and the placement of an object within the tunnel, whereby the second portion is of a diameter which is equal to or less than the internal diameter of the object to be placed in the tunnel, such that the second portion can be inserted into the said object and the said object can be secured to the tip at the third portion.

Preferably, said first portion is configured to create a tunnel in a medium through which it is passed, in use.

More preferably, said first portion is configured to create a tunnel with an internal diameter substantially equal to the external diameter of a tubular object to be placed in said tunnel.

Preferably, the maximum diameter of said second portion is configured to equal the internal diameter of a said tubular object to be placed in said tunnel.

Preferably, said third portion is configured for attachment of a said tubular object to be placed in said tunnel.

Preferably, said attachment means comprises a threaded shaft. Alternatively, said attachment means is a Luer lock component.

Preferably, said second portion comprises a rounded nose.

Preferably, said third portion is located approximately mid-way along the length of said tip.

In accordance with a second aspect of the present invention there is provided a handle for a tunnelling instrument, wherein said handle is configured to be attached to and detached from a tunneller shaft of a tunnelling instrument, at any point along the length of the tunneller shaft.

This particular handle construction has the advantage of providing extra control and more accurate steering of a tunneller shaft, particularly when a long tunneller shaft is employed. This is because the handle can be attached at point along the length of the tunneller shaft. A further advantage is that there is no need to remove any end fittings, such as tips, from the tunneller shaft in order to attach the handle. This saves time, simplifies the tunnelling procedure and eliminates the risk of the end fittings being lost and subsequently replaced with an incorrect part.

Preferably, said handle is formed from flexible material.

Preferably, said handle comprises a substantially cylindrical body with a longitudinal slit penetrating radially through the body to approximately the centre of the body.

Preferably, said handle has an inner surface configured to grip said tunneller shaft, in use.

Preferably, said handle has an outer surface configured to be gripped by an operator, when in use.

In accordance with a third aspect of the present invention there is provided a tunnelling instrument comprising: a pair of tips, each having an attachment means; a connection means for forming a link between said tips; and a tunneller shaft slidably engagable with said connection means and having complementary attachment means at either end thereof for selective attachment to the attachment means of each of said tips.

This tunnelling instrument has the advantage that, due to the connection means, the appropriate tips are always readily available for quick attachment to the tunneller shaft. Thus, eliminating the risk of losing or incorrectly replacing the tips after they have been detached from the tunneller shaft. In addition, bidirectional tunnelling is permitted.

Preferably, one of said tips is a tip in accordance with the first aspect of the invention.

Preferably, each of said tips is a tip in accordance with the first aspect of the invention.

Preferably, each of said tips have substantially the same dimensions.

Alternatively, each of said tips have different dimensions.

Preferably, said connection means is flexible.

More preferably, said connection means is in the form of a cord.

Preferably, said connection means includes a lumen. Preferably, said lumen extends from the distal end of one of said tips, through said connection means, to the distal end of the other of said tips. More preferably, said lumen is configured for the passage of a device, substance or energy.

Preferably, said connection means is configured for detachment from the tunnelling instrument.

Preferably, said connection means is configured as a catheter.

More preferably, said connection means is configured as a device for use in medical therapy, diagnostic purposes or surgery.

Preferably, said connection means is configured as a biologically absorbed device.

Preferably, said connection means has a length of at least twice the length of said tunneller shaft.

Preferably, said tunneller shaft comprises a plurality of discrete components.

Preferably, said tunneller shaft is hollow to allow said connection means to pass therethrough.

Preferably, said tunneller shaft includes a longitudinal slit to allow said connection means to be inserted into and removed from said tunneller shaft.

Preferably, said tunnelling instrument further comprising a handle.

Preferably, said handle is a handle in accordance with the second aspect of the invention.

Preferably, at least a part of said tunnelling instrument is provided within a protective sheath.

Preferably, at least a part of said tunnelling instrument is coated with biological or pharmaceutical agents.

In accordance with a fourth aspect of the present invention there is provided a tunnelling kit comprising: a tunnelling instrument in accordance with the third aspect of the invention; and one or more additional tips, each having an attachment means.

This tunnelling kit has the same advantages as the tunnelling instrument plus the additional advantage that the tips can be selected or mixed and matched to suit the particular requirements of the job.

Preferably, each of said additional tips is a tip in accordance with the first aspect of the invention.

Preferably, said tips are provided in a range of different dimensions.

Preferably, the tunnelling kit comprises a range of tips having first portions with different greatest diameters.

Preferably, the tunnelling kit comprises a range of tips having second portions with different maximum diameters.

Preferably, the tunnelling kit comprises a range of tips having third portions of different diameters.

Preferably, said tips include markings related to their dimensions.

Preferably, said tips are colour coded in accordance with their dimensions.

Preferably, the tunnelling kit further comprises one or more additional connection means for forming a link between two of said tips.

Preferably, the tunnelling kit further comprises one or more additional tunneller shafts, which are slidably engagable with said connection means and have complementary attachment means at either end thereof for selective attachment to the attachment means of said tips.

The present invention also relates to the use of a tunnelling instrument in accordance with the third aspect of the invention, for the creation of a tunnel.

In addition, the present invention relates to the use of a tunnelling instrument in accordance with the third aspect of the invention, for the placement of an object within a tunnel.

Further, the present invention relates to the use of a tunnelling instrument in accordance with the third aspect of the invention, for the creation of a tunnel and subsequent placement of an object within said tunnel.

BRIEF DESCRIPTION OF THE DRAWINGS

Particular embodiments of the various aspects of the invention are illustrated in the accompanying drawings wherein:

FIG. 2A shows a side view of two tips according to the first aspect of the invention connected to a connection means according to the third aspect of the invention, plus an end view of the above and a juxtaposed tubular object;

FIG. 2B shows a side cross-sectional view of a tunneller shaft according to the third aspect of the invention, plus an end view of the above;

FIG. 2C shows a side view of a handle according to the second aspect of the invention, plus an end view of the above;

FIG. 3 shows the components of FIGS. 2A-C assembled into a tunnelling instrument according to the third aspect of the invention;

FIGS. 4A through 4G illustrate use of a tunnelling instrument as shown in FIG. 3;

FIGS. 5A through 5H illustrate an alternative use of a tunnelling instrument as shown in FIG. 3; and FIGS. 6A through 6H illustrate a further use of a tunnelling instrument as shown in FIG. 3.

DETAILED DESCRIPTION OF THE INVENTION

Figure 1:
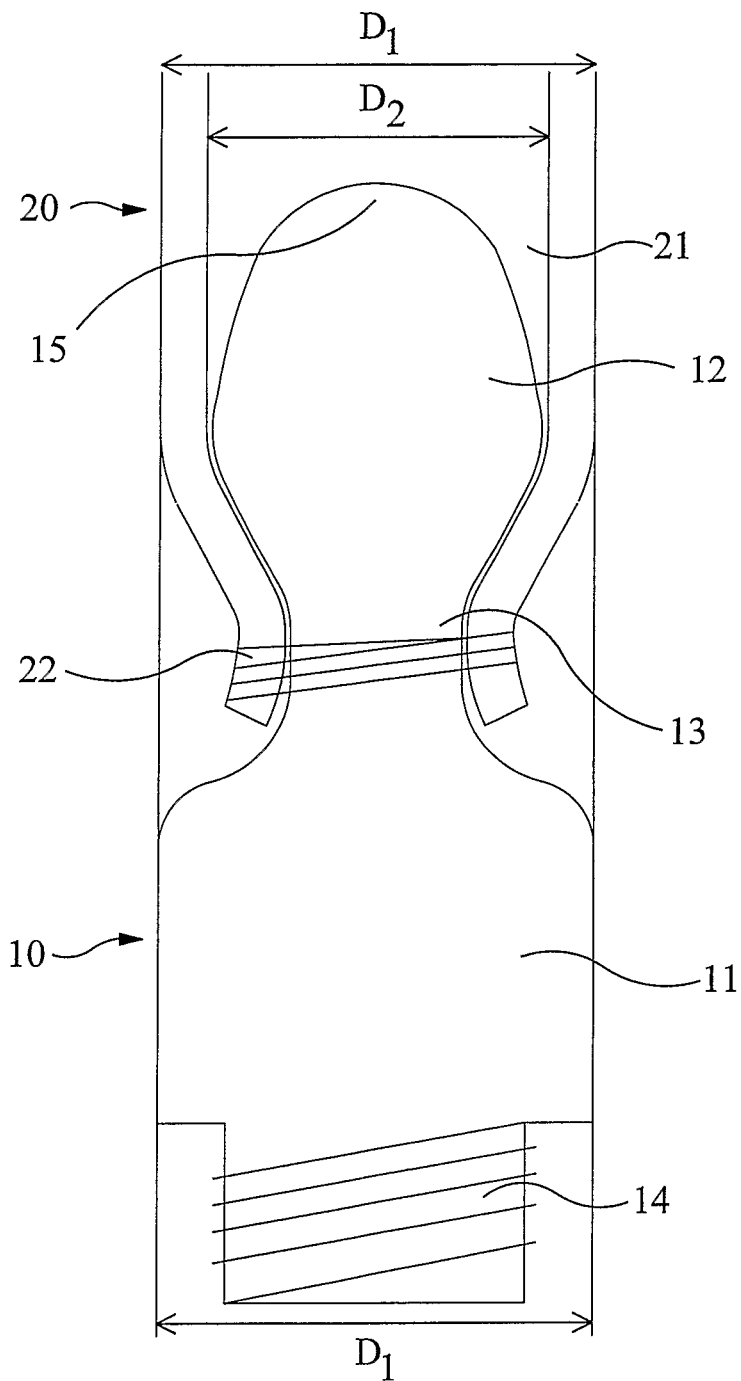
FIG. 1 is an enlarged view of a tip according to the first aspect of the present invention, with a tubular object attached.

Referring to the drawings, a tip 10 according to the first aspect of the invention is shown in FIG. 1. The tip 10 comprises an attachment means 14 in the form of a threaded shaft, a first portion 11 proximal to the attachment means 14, a second portion 12 distal to the attachment means 14, and a third portion 13 disposed between the first portion 11 and the second portion 12.

The attachment means 14 is configured for attaching the tip 10 to a tunnelling instrument 30, as shown in FIG. 3. The first portion 11 includes the greatest diameter $D_1$ of the tip 10. The second portion 12 has a maximum diameter $D_2$, which is less than the maximum diameter $D_1$ of the first portion 11. The third portion 13, as illustrated, has a diameter of less than the second portion 12. Thus, the third portion 13 forms a waist in the tip 10, between the second portion, or head, 12 and the first portion, or body, 11.

As shown in FIG. 1, a tubular object 20 is attached to the tip 10. The tubular object 20 may be any suitable tubular object that is desired to be placed within a tunnel. Thus, the tubular object 20 may be a graft, a catheter or a tubular device. The head 12 of the tip 10 is inserted into a cavity 21 formed in the tubular object 20. The internal diameter of the tubular object 20 is substantially equal to the maximum diameter $D_2$ of the head 12. Consequently, the head 12 forms a tight fit within the tubular object 20. For added security, the end of the tubular object 20 is attached to the tip 10 at the waist 13. In this instance, the end of the tubular object 20 is tied to the waist 13 by a line 22. The line 22 may be any suitably sized piece of ribbon, cord, string or tape. Conveniently, for medical applications, the line 22 is often suture material. Instead of a line, a suitable clip (not shown) may be used. This may be such as an O-ring preloaded onto a cylindrical former and slid off into the waist portion 13 (FIG. 1) once the tubular device has been correctly located onto the tunneller tip.

The body 11 of the tip 10 is configured to create a tunnel in any medium through which it is passed, in use. A particular application is in the creation of a subcutaneous tunnel and subsequent placement of an object in the subcutaneous tunnel. Thus, the body 11 is configured to create a tunnel with an internal diameter substantially equal to the maximum diameter $D_1$ of the body 11, which in turn is configured to be substantially equal to the external diameter of the tubular object 20 to be placed in the tunnel.

The head 12 of the tip 10 has a rounded end portion or nose 15. This is useful for ease of insertion of the tip 10 into the tubular object 20 and also helps in the separation of the medium during the creation of a tunnel therethrough.

As illustrated in FIG. 1, the waist 13 is located approximately mid-way along the length of the tip 10. As explained above, the waist 13 allows for the attachment of the tubular object 20 to the tip 10, at this point. Thus, when the tubular object 20 is attached to this point, the typically encountered ploughing effect, whereby the tubular object 20 scrapes along the tunnel wall, is reduced.

Although not shown, it is possible for the waist 13 to be of substantially equal diameter to the maximum diameter $D_2$ of the head 12. This construction provides a shelf, as opposed to a recess, for the attachment of the tubular object 20.

FIG. 2A shows two identical opposed tips 10, similar to the tip 10 shown in FIG. 1, with a connection means in the form of a cord 40 between the ends of the two tips 10 adjacent to the attachment means 14. The cord 40 is preferably flexible and is attached to the tips 10 by any suitable means, for example, by bonding or by being tied to a convenient point on the tip 10 (not shown). The cord 40 may be provided with a lumen (not shown) therethrough, thus, allowing for the injection of fluids or for suction. These options may assist with the tunnelling procedure and they can be used to re-hydrate native tissue if it is being placed in the body. Also shown in FIG. 2 is an end view of one of the tips 10 attached to the cord 40. This shows the difference between the maximum diameters of both the head 12 and the body 11. Adjacent this view is a cross-sectional illustration of part of a tubular object 20. Thus, it can be seen that the maximum diameter $D_2$ of the head 12 is substantially equal to the internal diameter of the tubular object 20 and the maximum diameter $D_1$ of the body 11 is substantially equal to the external diameter of the tubular object 20.

A tunneller shaft 50 according to the third aspect of the present invention, is shown in both side and end cross-sectional views in FIG. 2B. Thus, the tunneller shaft 50 is in the form of a relatively rigid and slightly curved cylindrical element 53 with a hollow interior 51. Each end of the tunneller shaft 50 includes an internal thread 52 configured for mating with the thread of a tip 10 as shown in FIG. 1. Other complementary attachment means 52, 14 may be provided on the ends of the tunneller shaft 50 and tip 10, if desired. This could be a Luer lock or an alternative method that requires a more minimal turning motion than a conventional thread affords.

A handle 60 according to one embodiment of the second aspect of the invention, is shown in both side and end cross-sectional views in FIG. 2C. The handle 60 is designed to be able to be attached to and detached from a tunneller shaft 50, like that shown in FIG. 2B, at any point along the length of the tunneller shaft 50. The handle 60 is formed from flexible material and has a substantially cylindrical body 61 with a longitudinal slit 62 penetrating radially through the body 61 to approximately the centre of the body 61, as shown. The handle 60 also includes an inner surface 63 configured to grip said tunneller shaft 50, in use, even in wet conditions. As such, the inner surface 63 may be roughened and/or may include projections or grooves (not shown) to aid with grip. Preferably, the outer surface 64 of the handle 60 is configured to be gripped by an operator, when in use. The handle 60 may be made from plastic, silicone or other materials and is designed to provide extra control over the tunneller shaft 50, particularly when a long tunneller shaft 50 is employed. The handle 60 according to the second aspect of the invention can also provide greater three-dimensional movement and control during a tunnelling procedure, should this be required. This is because the handle 60 can grip the end of a tunneller shaft 50 or any point along the length of the tunneller shaft 50 thereby allowing more steering possibilities for the rigid tunneller shaft 50 as it proceeds along its chosen path in the body.

A tunnelling instrument 30 in accordance with the third aspect of the invention is shown in FIG. 3. As illustrated, this comprises the assembly of the components shown in FIGS. 2A, 2B and 2C. Thus, the cord 40, connected to opposed tips 10, is passed through the hollow interior 51 of the tunneller shaft 50. The removable handle 60 is wrapped around the tunneller shaft 50. The tunneller shaft 50, with or without the attached handle 60, is designed to be slidable along the length of the cord 40 between the opposed tips 10. Consequently, each end of the tunneller shaft 50 may be selectively attached to the adjacent tip 10 by means of the corresponding attachment elements 14 and 52. Thus, the tunnelling instrument 30 is configured for bi-directional tunnelling. As shown in FIG. 3, the tunneller shaft 50 is attached by complementary screw threads 14 and 52 to the lower tip 10.

Figure 4F:
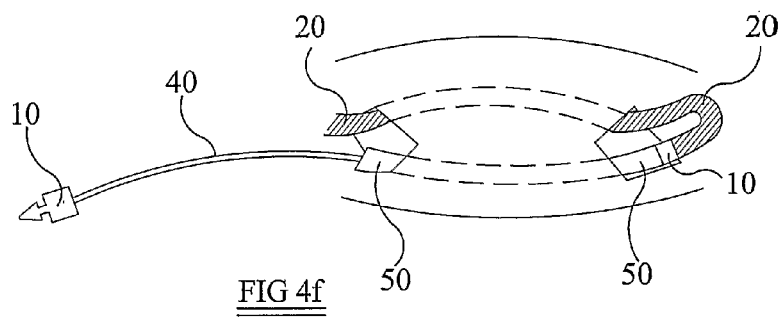
Figure 4G:
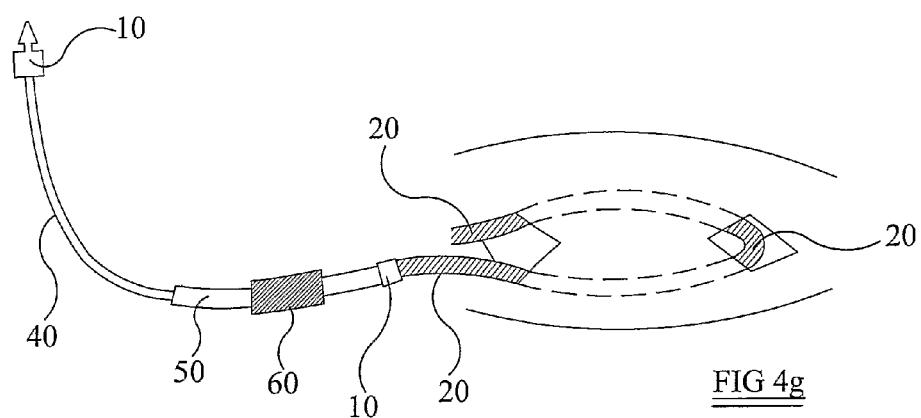

An example of use of the tunnelling instrument 30 of FIG. 3, is illustrated in FIGS. 4A through 4G. In this example, part of a limb 70 is depicted but the same procedure may be carried out on any object through which a tunnel is to be made and/or an object is to be placed therein. As shown in FIG. 4A, the limb 70 is provided with an appropriate entry site 71 and desirable exit site 72. These sites 71, 72 may be prepared in a preliminary stage (not shown) wherein the necessary incisions are made. The dashed channels 73 in FIGS. 4A through 4G represent the paths of the proposed as well as actual tunnels created within the limb 70. The first stage of the procedure is to introduce a tunnelling instrument 30, according to the present invention, into the entry site 71. As shown in FIG. 4A, the tunnelling instrument is initially configured as shown in FIG. 3 and is fed into the entry site 71 with the end of the tunneller shaft 50 that is attached to the tip 10 being introduced first. The handle 60 is conveniently employed on the tunneller shaft 50 at this stage, to assist with the manipulation of the tunnelling instrument 30 as it is forced through the subcutaneous tissue in the limb 70 to form a tunnel 73. If desired the handle 60 may be progressively moved along the length of the tunneller shaft 50 towards the rear of the tunnelling instrument 30 as the tunneller shaft 50 is fed into the limb 70. Depending on the length of the tunneller shaft 50 and the length of the tunnel to be created, it may be necessary or desirable to remove the handle 60 from the portion of the tunneller shaft 50 adjacent the entry site 71 and to reattach the handle 60 to the portion of the tunneller shaft 50 emerging from the exit site 72. The handle 60 can then be used to assist in pulling through the tunnelling shaft 50 as opposed to pushing it through. It may not, however, be necessary to pull the tunnelling shaft 50 completely through the limb 70. Instead, it may be more desirable to attach the tubular object 20, which is to be placed in the tunnel 73, to the tip 10 once it has emerged sufficiently from the exit site 72. This is shown in FIG. 4B. The tubular object 20 is attached to the tip 10 at the waist 13, as shown in FIG. 1. The tunnelling instrument 30 is then pulled back through the tunnel 73 until the end of the tubular object 20 emerges from the entry site 71, as shown in FIG. 4C. The tunneller shaft 50 is then unscrewed from the tip 10, which is still attached to the tubular object 20. The tunneller shaft is then slid along the cord 40 and attached to the tip 10 at the opposite end of the cord 40. The tip 10, with the tunneller shaft 50 attached, is then fed into the entry site 71, as shown in FIG. 4D. As before, a second tunnel 73 is created in the limb 70 as the tunneller shaft 50 is fed therethrough. Once the tip 10 emerges from the exit site 72, as shown in FIG. 4E, it is unscrewed and pulled away from the tunneller shaft 50 in order to draw the cord 40 through the tunneller shaft 50 until the opposed tip 10, attached to the tubular object 20, abuts the rear end of the tunneller shaft 50. The tip 10, attached to the tubular object 20, is then screwed onto the rear of the tunneller shaft 50 as shown in FIG. 4F. Pulling the tunnelling shaft 50 out of the exit site 72 then draws the tubular object 20 through the second tunnel 73, as shown in FIG. 4G. The handle 60 may be reattached to the tunneller shaft 50 to assist in pulling the tubular object through the tunnel 73. Once the end of the tubular object 20 has emerged from the exit site 73 it is detached from the tip 10 and the respective ends of the tubular object 20 can be anastomosed to the necessary anatomical structures at each end.

Figure 5A:
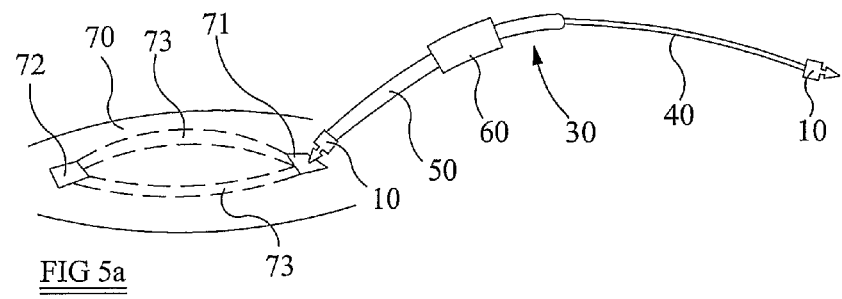
Figure 5B:
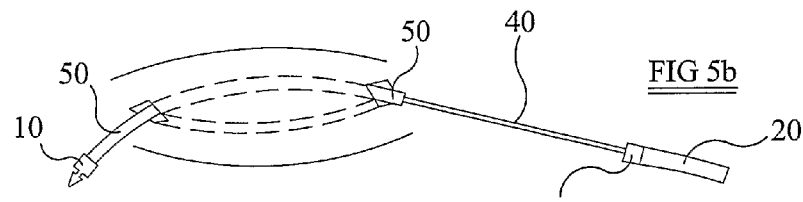
Figure 5C:
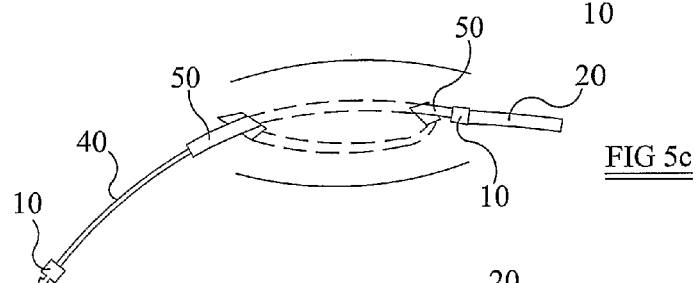
Figure 5D:
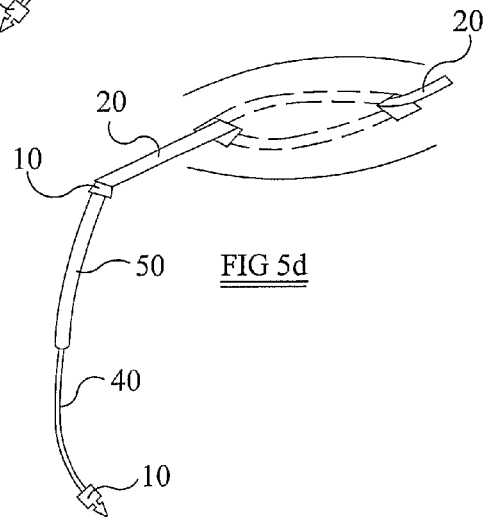

An example of an alternative use of the tunnelling instrument 30 of FIG. 3, is illustrated in FIGS. 5A through 5H. As above, the illustration relates to tunnelling in a limb 70 with an entry site 71 and an exit site 72. As in FIG. 4A, FIG. 5A shows the introduction of the tunnelling instrument 30 into the entry site 71, with the tip 10 attached to the tunnelling shaft 50 being introduced first. Once more, the removable handle 60 is attached to the tunnelling shaft 50 to assist with the manipulation of the tunnelling instrument 30. When the leading tip 10 emerges from the exit site 72, a tubular object is attached to the trailing tip 10, as shown in FIG. 5B. The leading tip 10 is then unscrewed and pulled away from the tunneller shaft 50 to draw the cord 40 through the tunneller shaft 50 until the trailing tip 10 abuts the rear end of the tunneller shaft 50. The trailing tip 10 is then attached to the tunneller shaft 50 at its rear end, as shown in FIG. 5C. The tunneller shaft 50 is then pulled completely through the limb 70 and out of the exit site 72, drawing with it the tubular object 20 attached to the trailing tip 10, as shown in FIG. 5D. The tunneller shaft 50 is then unscrewed from the trailing tip 10, which is still attached to the tubular object 20, and screwed onto the leading tip 10 for re-insertion into the exit site 72, as shown in FIG. 5E. The provision of a flexible cord 40 creates 'slack' to allow the manipulation of the tunneller shaft 50 into a suitable position for re-entry into the exit site 72. The leading tip 10 and attached tunneller shaft 50 are then fed through the limb 70 to create a second tunnel 73, as shown in FIG. 5F. When the leading tip 10 emerges from the entry site 71, it is unscrewed and pulled away from the tunneller shaft 50. This draws the cord 40 through the tunneller shaft 50, which in turn draws the trailing tip 10, still attached to the tubular object 20, to abut the rear of the tunneller shaft 50. The trailing tip 10 is then attached to the rear of the tunneller shaft 50, as shown in FIG. 5G. Finally, the tunneller shaft 50 is pulled completely out of the entry site 71 to draw the tubular object 20 through the second tunnel 73, as shown in FIG. 5H. As before, the handle 60 may be reattached to the tunneller shaft 50 to assist with this stage. The end of the tubular object is then detached from the tip 10 so that the respective ends of the tubular object 20 can be anastomosed to the necessary anatomical structures at each end.

Figure 6C:
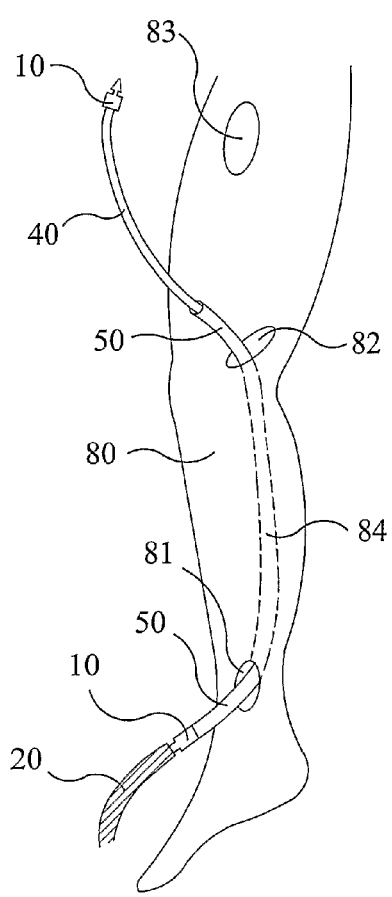
Figure 6D:
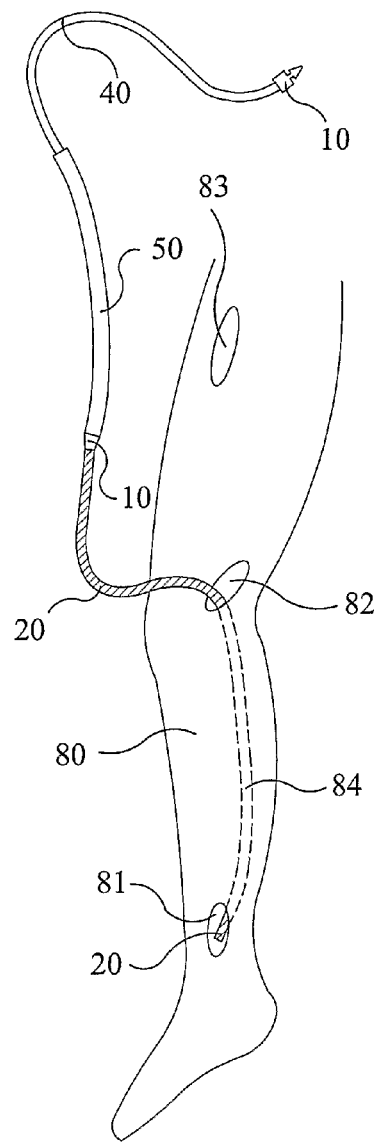
Figures 6E, 6F:
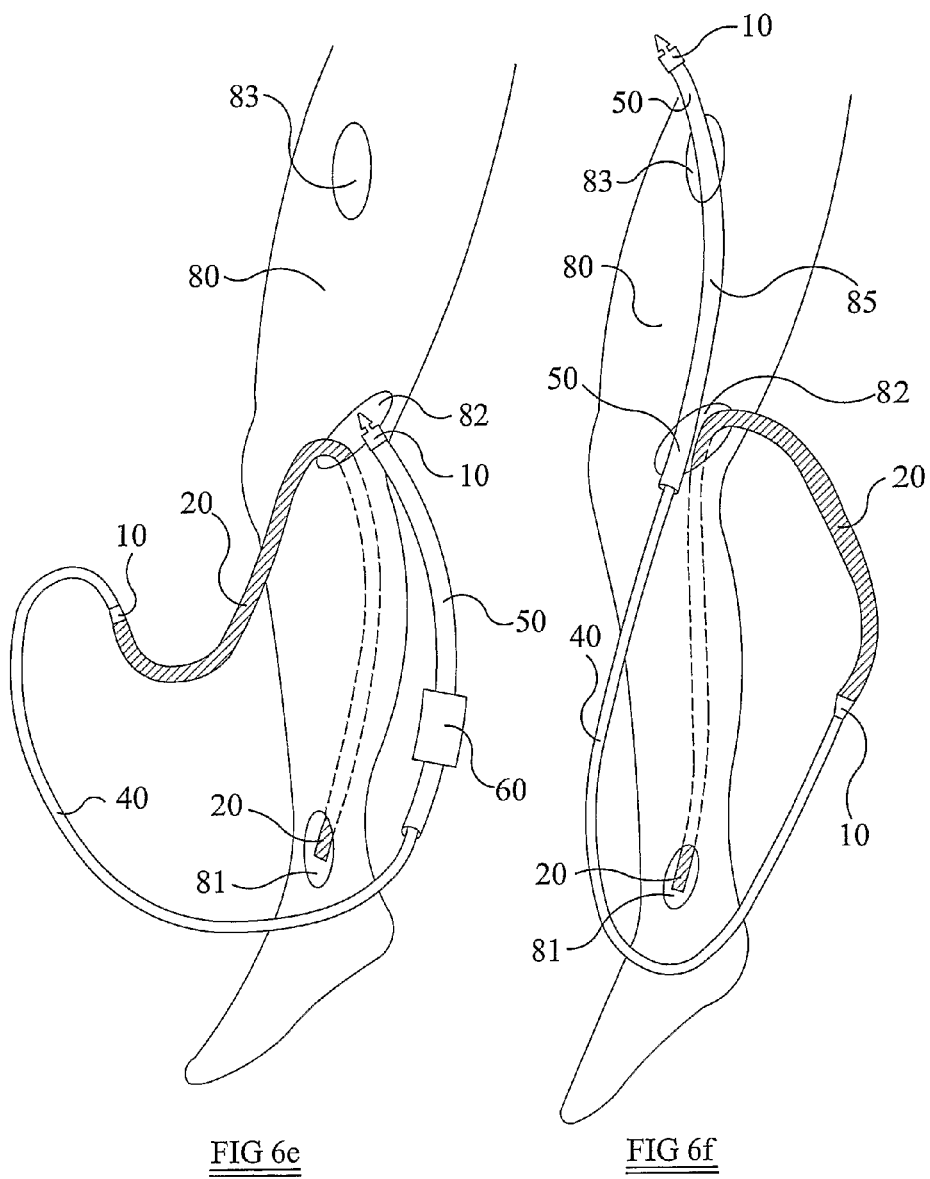

A further example of use of the tunnelling instrument 30 of FIG. 3, is illustrated in FIGS. 6A through 6H. More specifically, FIGS. 6A through 6H relate to continual multi incisional tunnelling. The example shown concerns the multi incisional tunnelling in a leg 80 having a distal incision 81, a mid incision 82 and a proximal incision 83, although the general technique could be applied to any body part or indeed any other object. As previously, the first step, shown in FIG. 6A, is the introduction of the tunnelling instrument 30 into the distal incision 81 with the leading tip 10 attached to the tunneller shaft 50. The tunneller shaft 50 is then pushed through the leg 80 until the leading tip 10 emerges from the mid incision 82, as shown in FIG. 6B. This action creates a tunnel 84 between the distal incision 81 and the mid incision 82, as illustrated. The tubular object 20 is then attached to the trailing tip 10 at its waist 13. The leading tip 10 is then unscrewed and pulled away from the tunneller shaft 50 to draw the cord 40 through the tunneller shaft 50 until the trailing tip 10, with attached tubular object 20, abuts the rear of the tunneller shaft 50. The trailing tip 10 is then attached to the rear of the tunneller shaft 50 as shown in FIG. 6C. The tunneller shaft 50 is then pulled completely out of the leg 80 through mid incision 82. This action draws the tubular object 20, attached to the trailing tip 10, through the tunnel 84 as shown in FIG. 6D. The trailing end of the tubular object 20 may have been already anastomosed to the desired structure distally prior to tunnelling. The tunneller shaft 50 is unscrewed from the trailing tip 10, which is still attached to the tubular object 20, and slid along the cord 40 to abut the leading tip 10. The leading tip 10 is attached to the tunneller shaft 50 and reintroduced to the mid incision 82, as shown in FIG. 6E, to form a tunnel 85 between the mid incision 82 and the proximal incision 83. Once the leading tip 10 has emerged from the proximal incision 83, as shown in FIG. 6F, it is unscrewed and pulled away from the tunneller shaft 50 to draw the cord 40 through the tunneller shaft 50 until the trailing tip 10 abuts the rear of the tunneller shaft 50. The trailing tip 10, with the tubular object 20 still attached, is then screwed onto the rear of the tunneller shaft 50, as shown in FIG. 6G. The tunneller shaft 50 is then pulled completely out of the leg 80 through the proximal incision 83. This in turn, draws the tubular object 20 through the tunnel 85 until it emerges from the proximal incision 83, as shown in FIG. 6H. The tubular object 20 is then detached from the trailing tip 10 to be anastomosed to a desired anatomical structure adjacent the proximal incision 83. The procedural steps outlined in FIGS. 6A through 6H may be continued if necessary, between further incisions.

Optionally, in any of the above procedures, the tubular object 20 may be placed over the tunneller shaft 50 or cord 40 to enable its placement.

The advantages of using the tunnelling instrument 30, according to the third aspect of the present invention, in any of the above procedures are that the tips 10 cannot become lost or replaced by incorrectly sized tips 10 during the procedure, due to attachment to the tunnelling instrument 30 via the cord 40 at all times; the tubular object 20 to be placed in the tunnel 73, 84, 85 needs only be attached to the tunnelling instrument 30 at the beginning of the procedure and detached from the tunnelling instrument 30 at the end of the procedure, as opposed to the current procedures which require multiple attachments/detachments; and the tips 10 do not need to be detached from the tunneller shaft 50 for the attachment of the handle 60. Thus, the tunnelling instrument 30 according to the third aspect of the invention is much safer, simpler and quicker to use than existing devices. By virtue of its versatility, it is also suitable for many different tunnelling activities. In addition, the flexible cord 40 can become a flexible trailing end of the tunnelling instrument 30, thus, enabling continuation of the tunnelling procedure especially when multiple tunnels 73, 84, 85 are required since it eliminates the need to attach and reattach the end of the tubular object 20 from the respective tip 10 and therefore provides continuity in placing a continuous tubular object 20. The provision of the flexible cord 40 also allows tunnelling and tubular object 20 placement in either direction and overcomes the physical constraints of traditional rigid tunnelling instruments. This is because traditional rigid tunnelling instruments cannot re-enter a second incision site when tunnelling in the same direction without either the removal of the tubular object from the tip to which it is attached, or the removal of the tip itself from the tunneller shaft. This is because the handle would need to be reattached to the trailing end of the tunneller shaft. Furthermore, even in the event that a handle was not used, there would be insufficient length of the tubular object to compensate safely.

The tunnelling instrument 30 may be supplied with additional tips 10 in a tunnelling kit (not shown), in accordance with the fourth aspect of the present invention. Preferably, differently sized tips 10 are provided in the kit to provide a range of diameters for both the creation of differently sized tunnels 73, 84, 85 and the attachment of differently sized tubular objects 20. Thus, the kit will include tips 10 suitable for a wide range of applications. It may be desirable to employ two differently dimensioned tips 10 in a particular application, for example, when creating a tunnel 73, 84, 85 with different dimensions at each end. This may be desirable in order to create a constriction in a tubular object 20. Similarly, a range of differently sized tunneller shafts 50 may be provided in the kit and these also may have varying dimensions along their length. Accordingly, differently sized cords 40 and handles 60 may be included.

The tunnelling kit may include the tubular device to be implanted pre-attached to the instrument during manufacture.

The individual components of tunnelling instrument 30 may be made from a variety of materials to suit circumstances. They may be configured from re-usable materials such as metal or may be made from disposable materials so that the instrument may be supplied sterile for only single patient use. In particular, the tunneller shaft 50 may be made of metal, plastic or a metal-plastic composite. The tunneller shaft 50 may be provided in a variety of lengths and may be straight or curved to any desired degree. Conveniently, the length of the cord 40 is at least twice the length of the tunneller shaft 50. This allows the tunnelling instrument 30 to be effectively folded in two and is useful when it is desired to exit and subsequently re-enter a respective site. Each of the components of the tunnelling instrument 30, including the tips 10, the cord 40, the tunneller shaft 50 and the handle 60, may include markings or be colour coded to identify their respective dimensions. The tips of the present invention are multi-purpose and include diameters configured both for the creation of a tunnel 73, 84, 85 and the attachment of a tubular object 20 to be placed in the tunnel 73, 84, 85.

The invention claimed is:

1. A tunnelling instrument for forming a subcutaneous tunnel comprising:
    a tunneller shaft having a hollow interior through which passes a flexible connector forming a link between a pair of tips,
    each tip having a positive attachment mechanism, and at least one tip having a first portion which is configured to create a subcutaneous tunnel, said first portion proximal to said attachment mechanism and having the greatest diameter of said tip; a second portion distal to said attachment mechanism and having a portion and said second portion and having a diameter of less than or equal to said second portion; and
    the tunneller shaft is slidable along the length of the connector between the tips, the tunneller shaft having a complementary attachment mechanism at each end thereof for selective attachment to the attachment mechanism of the adjacent tips, thereby permitting bi-directional tunneling without the need to detach the tips from the connector.

2. A tunnelling instrument as claimed in claim 1 wherein each of said tips have different dimensions.

3. A tunnelling instrument as claimed in claim 1 wherein said connector includes a lumen.

4. A tunnelling instrument as claimed in claim 3 wherein said lumen extends from the distal end of one of said tips, through said connector, to the distal end of the other of said tips.

5. A tunneling instrument as claimed in claim 3 wherein said lumen is configured for the passage of a device, substance or energy.

6. A tunnelling instrument as claimed in claim 1 wherein said connector is configured as a catheter.

7. A tunnelling instrument as claimed in claim 1 wherein said connector is configured as a device for use in medical therapy, diagnostic purposes or surgery.

8. A tunnelling instrument as claimed in claim 1 wherein said connector is configured as a biologically absorbed device.

9. A tunnelling instrument as claimed in claim 1 wherein said connector has a length of at least twice the length of said tunneller shaft.

10. A tunnelling instrument as claimed in claim 1 further comprising a handle.

11. A tunnelling instrument as claimed in claim 1 wherein at least a part of said tunneling instrument is provided within a protective sheath.

12. A tunnelling instrument as claimed in claim 1 wherein at least a part of said tunneling instrument is coated with biological or pharmaceutical agents.

13. A tunnelling kit comprising:
    a tunneling instrument of claim 1; and
    one or more additional tips, each having an attachment mechanism.

14. A tunnelling kit as claimed in claim 13 wherein said tips are provided in a range of different dimensions.

* * * * *